US00PP15120P2

(12) United States Plant Patent
Olesen et al.

(10) Patent No.: US PP15,120 P2
(45) Date of Patent: Aug. 31, 2004

(54) MINIATURE ROSE PLANT NAMED 'POULRA028'

(50) Latin Name: *Rosa hybrida*
Varietal Denomination: POULra028

(75) Inventors: L. Pernille Olesen, Fredensborg (DK); Mogens N. Olesen, Fredensborg (DK)

(73) Assignee: Poulsen Roser A/S, Fredensborg (DK)

( * ) Notice: Subject to any disclaimer, the term of this patent is extended or adjusted under 35 U.S.C. 154(b) by 0 days.

(21) Appl. No.: 10/719,713

(22) Filed: Nov. 21, 2003

(51) Int. Cl.[7] ..... A01H 5/00
(52) U.S. Cl. ..... Plt./116
(58) Field of Search ..... Plt./116

*Primary Examiner*—Anne Marie Grunberg
*Assistant Examiner*—S. B. McCormick-Ewoldt

(57) ABSTRACT

A new miniature rose plant which has abundant, red and yellow bicolor flowers and attractive foliage. The variety successfully propagates from softwood cuttings and is suitable for year round production in commercial glasshouses. This new and distinct variety has shown to be uniform and stable in the resulting generations from asexual propagation.

1 Drawing Sheet

Botanical classification: *Rosa hybrida.*
Variety denomination: 'POULra028'.

SUMMARY OF THE INVENTION

The present discovery constitutes a new and distinct variety of a miniature pot rose plant which was discovered in a cultivated area. The mutation resulted from 'POULmist', a miniature pot rose hybridized by the same inventors. 'POULmist' is described and illustrated in U.S. Plant patent application Ser. No. 09/655,262, dated Sep. 5, 2000. The new rose variety resulted from a naturally occurring mutation of unknown causation on a branch of 'POULmist'.

The rose plant of the present discovery has a unique combination of characteristics which are outstanding in the new variety and which distinguish it from the original rose 'POULmist'. For example, while flowers of 'POULmist' are yellow, flowers of 'POULra028' are red and yellow bi-color.

This combination of qualities is not present in previously available commercial cultivars of this type, known to the inventors, and distinguish 'POULra028' from all other varieties of which we are aware. For example, the new variety has:

1. Uniform and abundant flowers;
2. Vigorous and compact growth;
3. Year-round flowering under glasshouse conditions;
4. Suitability for production from softwood cuttings in pots;
5. Durable flowers and foliage which make a variety suitable for distribution in the floral industry.

The resulting mutation was selected and evaluations were conducted on the resulting rose plants in a controlled environment.

Asexual reproduction of 'POULra028' by cuttings and traditional budding was first done by L. Pernille and Mogens N. Olesen in their nursery in Fredensborg, Denmark in 1996. This initial and other subsequent propagations conducted in controlled environments have demonstrated that the characteristics of 'POULra028' are stable and reproduced true to type in successive generations of asexual reproduction.

BRIEF DESCRIPTION OF THE DRAWING

The accompanying color illustration shows as true as is reasonably possible to obtain in color photographs of this type, the typical characteristics of the buds, flowers, leaves, and stems of 'POULra028'. Specifically illustrated in FIG. 1:

FIG. 1.1; Flowers at various stages of opening;

FIG. 1.2; Stem showing branching and the attachment of leaves and peduncle;

FIG. 1.3; Flower petals, detached;

FIG. 1.4; Sepals, receptacle, and pedicel;

FIG. 1.5; Mature and juvenile leaves;

FIG. 1.6; Bare stem exhibiting thorns.

DETAILED DESCRIPTION OF THE VARIETY

The following is a description of 'POULra028', as observed in its growth in glasshouses in Fredensborg, Denmark. Observed plants are 21 weeks of age, and were cultivated in a 10 cm pot. Color references are made using The Royal Horticultural Society (London, England) Colour Chart, 1995, except where common terms of color are used.

For a comparison, several physical characteristics of the rose variety 'POULrosit', a rose variety from the same inventors described and illustrated in U.S. Plant Pat. No. 13,111, issued on Oct. 22, 2002 are compared to 'POULra028' in Chart 1.

CHART 1

| | 'POULra028' | 'POULrosit' |
|---|---|---|
| General Tonality | Yellow Group 13C with distinct intonations of Red Group 33B. | Yellow Group 4A and 4D. Petal margins Red Group 52A. |
| Bud Color | Yellow Group 13C, with distinct intonations Red 43A. | Red Group 45B, with intonations of Yellow 12B. |
| Petalage | Very Double, .80 to 85 petals. | Double, 23 to 25 petals. |

FLOWER AND FLOWER BUD

Blooming habit: Continuous.

Flower bud:

*Size.*—From base of receptacle to top of the flower bud, 28 mm in length. With sepal extension bud is 30 mm in length. Flower bud diameter is 20 mm.

*Bud form.*—Pointed ovoid to globular.

*Bud color.*—As sepals unfold, flower bud is Yellow Group 13C with distinct intonations of Red Group 43A, 5 to 6 mm from petal margins. Colors blend at 4 to 5 mm from the margin. At ¼ opening, Yellow Group 13C with distinct intonations of Red Group 43A, 5 to 6 mm from petal margins. Colors blend at 4 to 5 mm from the margin.

Sepals:

*Upper surface.*—Color: Green Group 137A to 139A.

*Lower surface.*—Color: Green Group 139A.

*Shape.*—Sepal apex is cirrhose. Base is flat at union with receptacle.

*Margins.*—Margins have medium foliaceous appendages on three of the five sepals. Appendages extend 8 to 9 mm from the sepals at the base. Surfaces of sepals are slightly pubescent. Observed stipitate glands are elongated, 1.5 mm, present in medium quantity.

*Size.*—35 mm (l)×5 mm (w). Width of sepals is 15 mm when measuring span of the foliaceous appendages.

Receptacle:

*Surface texture.*—Smooth.

*Shape.*—Urn-shaped.

*Size.*—7 mm (h)×8 mm (w).

*Color.*—Yellow-Green Group 144A.

*Anthocyanin.*—None observed.

Peduncle:

*Surface.*—Smooth with no stipitate glands.

*Length.*—23 mm average length.

*Color.*—Yellow-Green Group 144A.

*Strength.*—Strong.

Borne: Singularly.

Flower bloom:

*Fragrance.*—None.

*Duration.*—The blooms have a duration on the plant of approximately 18 days. Petals fall cleanly away from plant.

*Size.*—Average flower diameter is 50 mm when open. Average flower depth is 23 mm.

*Form.*—General shape is high centered and somewhat globular upon opening. When fully open flowers form an imbricated rosette with outer petals overlapping and strongly reflexed.

Shape of flower when viewed from the side: Upon opening, upper part:Flat. Upon opening, lower part:Flat. Open flower, upper part: Flattened convex. Open flower, lower part: Concave.

*Petalage.*—Average range: 80 to 85 petals under normal conditions with 15 petaloids.

Color:

*Upon opening, petals.*—Outermost petals: Outer Side: Yellow Group 13C. Blending with Red Group 43A, 5 cm from petal margins, becoming completely Red Group 43A at the petal margin. Inner Side: Yellow Group 7A. Blending with Red Group 43A, 5 cm from petal margins. Innermost petals: Outer Side: Yellow Group 13C. Blending with Red Group 43A at 1 to 2 mm from petal margins. Inner Side: Yellow Group 7A, blending with Red Group 43A at 1 to 2 mm from petal margins.

*Upon opening.*—No distinctive coloration at petal base observed.

*After opening, petals.*—Outermost petals: Outer Side: Yellow Group 12C. Blending with Red Group 43A at outer 1 to 2 mm of margin. Inner Side: Yellow Group 7A. Blending with Red Group 43A at outer 1 to 2 mm of margin. Innermost petals: Outer Side: Yellow Group 13C. Blending with Red Group 43A at outer 0.5 mm of margin. Inner Side: Yellow Group 7A. Blending with Red Group 43A at outer 1 to 2 mm of margin.

*After opening.*—No distinctive coloration at petal base observed.

General tonality: On open flower Yellow Group 13C with distinct coloration of the Red Group 33B. After 10 to 12 days the color was Yellow Group 13C and distinct intonations of Red Group 50A.

Petals:

*Petal reflex.*—Upon opening: Petals reflex slightly. After opening: Outer petals reflexed strongly. Inner petals reflexed slightly.

*Petal margin.*—Entire and pointed in the center.

*Shape.*—Base Shape is acute. Apex shape is round.

*Size.*—18 to 21 mm (l)×12 to 22 mm (w).

*Thickness.*—Average.

*Arrangement.*—Not formal.

Petaloids:

*Quantity.*—15 to 18.

*Size.*—10 mm (l)×5 mm (w).

*Shape.*—Irregular.

*Color.*—Yellow Group 7A. Blending with Red Group 43A at petaloid margins.

Reproductive organs:

*Female.*—Pistils: Length: 6 mm long. Quantity: 38 (actual count). Stigmas: Color: Yellow-Green Group 145B. Styles: Color: Yellow-Green Group 145B.

*Male.*—Flowers are self sterile. Male reproductive parts are not developed.

*Seed formation.*—No seed formation observed.

PLANT

Plant growth: Vigorous, compact, upright to bushy. When grown as a 10 cm pot plant, the average height of the plant itself is 15 to 18 cm and the average width is 10 to 15 cm.

Stems:

*Internodal distance.*—18 to 15 mm (average).

*Length of stems.'*Average length 13 cm from flower to first branch. Stem diameter is 2 mm.

*Surface texture.*—Young wood: Smooth. Older wood: Smooth.

Plant foliage: Normal number of leaflets on normal leaves in middle of the stem: 7 leaflets.

*Compound leaf size.*—70 mm (l)×40 mm (w).

*Quantity.*—6 leaves per 10 cm of stem.

*Color.*—Juvenile foliage: Upper Leaf Surface is Yellow-Green Group 144A. Lower Leaf Surface is Yellow-Green Group 144B. Mature foliage: Upper Leaf Surface is Yellow-Green Group 147A. Lower Leaf Surface is Yellow-green Group 147B. Anthocyanin intonation: Location: Upper side of margins of juvenile leaflets. Color: Greyed-Red Group 179A.

Plant leaves and leaflets:

*Stipules.*—Size: 10 mm long. Shape: Linear, slightly broad based with outward extending apecies extend 5 mm. Margins: Finely serrated with stipitate glands. Stipitate glands in medium quantity. Color: Yellow-Green Group 147A.

*Petiole.*—Length: 10 to 13 mm. Color: Yellow-Green Group 146A. Underneath: Yellow-Green Group 144B.

*Rachis.*—Size: 30 mm. Color: Yellow-Green Group 144B. Underneath: Yellow-Green Group 146A. Stipitate glands few in quantity.

*Leaflet.*—Size: 27 mm (l)×19 mm (w). Edge: Serrated. General Shape: Elliptical. Apex Shape: Acute to cuspidate. Base Shape: Acute. Texture: Smooth. Arrangement: Odd pinnate. Venation: Reticulate. Leaf Gloss: Moderately glossy. Thickness: Medium.

Disease resistance: Average resistance to mildew, black spot, and Botrytis under normal growing conditions in Fredensborg, Denmark.

What is claimed is:

1. A new and distinct variety of rose plant of the miniature class, substantially as herein illustrated and described as a distinct and novel rose variety due to its abundant yellow and red bicolor flowers, vigorous growth, compact habit, suitability for production from softwood cuttings in pots, and durable flowers and foliage which make the variety suitable for distribution in the floral industry.

* * * * *

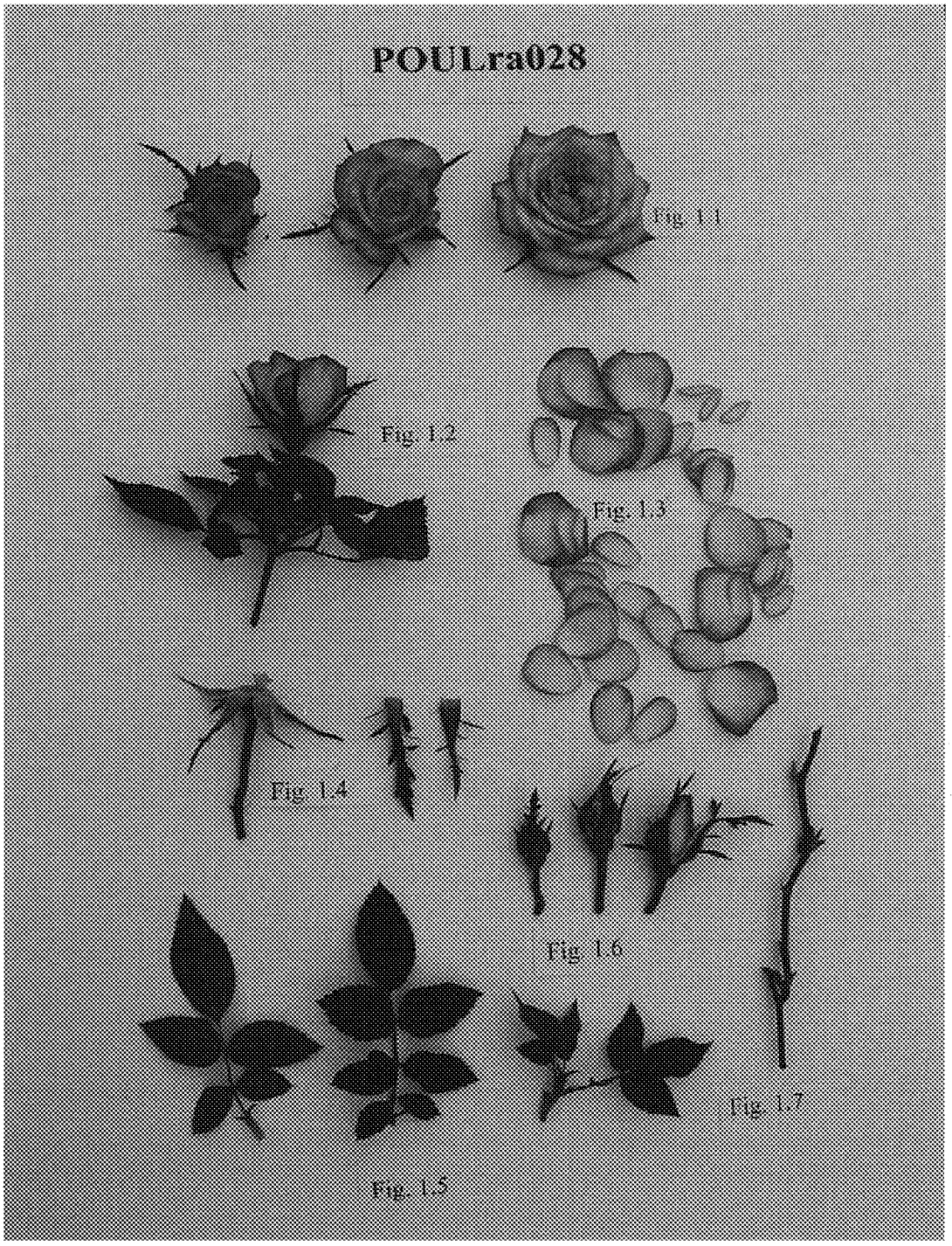
POULra028
Fig. 1.1
Fig. 1.2
Fig. 1.3
Fig. 1.4
Fig. 1.6
Fig. 1.7
Fig. 1.5